United States Patent [19]

Weiss et al.

[11] 4,383,733
[45] May 17, 1983

[54] DEVICE FOR FORMING LAYER IMAGES OF A THREE-DIMENSIONAL OBJECT BY MEANS OF A LENS MATRIX

[75] Inventors: Hermann Weiss, Hamburg; Erhard Klotz, Halstenbek; Ulf Tiemens, Prisdorf; Rolf Linde, Haseldorf; Wilfried Mauser, Hamburg, all of Fed. Rep. of Germany

[73] Assignee: U.S. Philips Corporation, New York, N.Y.

[21] Appl. No.: 196,233

[22] Filed: Oct. 14, 1980

[30] Foreign Application Priority Data

Oct. 30, 1979 [DE] Fed. Rep. of Germany ....... 2943758

[51] Int. Cl.³ ...................... G02B 27/22; G03B 35/06
[52] U.S. Cl. .................................... 350/130; 350/6.3; 378/41
[58] Field of Search ............... 350/130, 131, 132, 136, 350/142, 6.3; 353/101; 352/86; 250/313, 314

[56] References Cited

U.S. PATENT DOCUMENTS 3,746,872 7/1973 Ashe et al. ......................... 250/313

Primary Examiner—Jon W. Henry
Attorney, Agent, or Firm—Paul R. Miller

[57] ABSTRACT

For the formation of layer images of a three-dimensional object, the object is irradiated from a large number of radiation source positions which are situated in one plane. Thus, a coded image of the object, consisting of individual perspective images, is formed. Subsequently, the coded image is illuminated and the perspective images thereof are superposed for the reconstruction of the object by means of a lens matrix which extends parallel to the plane of the coded image and whose flat lens distribution corresponds to the distribution of the radiation source positions. In the superposition zone of the perspective images, a photosensitive element is introduced in order to form individual layer images of the object. For the formation of the different layer images on the photosensitive element, the lens matrix is displaced in the direction of the optical axis, and the photosensitive element is positioned each time within the depth of focus range of the lenses of the lens matrix.

6 Claims, 6 Drawing Figures

DEVICE FOR FORMING LAYER IMAGES OF A THREE-DIMENSIONAL OBJECT BY MEANS OF A LENS MATRIX

The invention relates to a device for examining the interior of a three-dimensional object which can be irradiated from a large number of radiation source positions which are situated in one plane in order to form a coded image which consists of separate perspective images, the perspective images of this coded image being superposed for the reconstruction of the object by means of a lens matrix which is arranged parallel to the plane of the coded image and whose lens distribution corresponds to the distribution of the radiation source positions, an image space thus being formed in which a photosensitive element can be introduced and displaced in order to form separate layer images of the object.

The lens matrix superposes the perspective images of the coded image so that in the image space of the lens matrix there is formed a three-dimensional brightness distribution which corresponds to the density distribution in the three-dimensional object. When a frosted glass plate, a film or an image pick-up tube is introduced into this image space, an image of arbitrary layers of the object, including oblique layers, can be formed, for example, by arranging the frosted glass plate at an angle. However, only layers of the object which are situated within the depth of focus range of the matrix lenses can be sharply imaged. Layer images reconstructed outside this range have a reduced image sharpness. In the case of a large reconstructed object volume and a fixed position of the lens matrix, therefore, a problem occurs in that not all layer images can be formed with the same sharpness. The depth of focus range can be increased by shielding of the matrix lenses, but such an increase is accompanied by a loss of intensity of the overlapping radiation beams, resulting in layer images of reduced intensity. Display of the layer image by means of a frosted glass plate, therefore, is only possible to a limited extent, and for the recording of the layer images on a film comparatively long exposure times are required.

The invention has for its object to provide a device whereby layer images of adequate intensity and uniform sharpness can be formed also of large objects.

This object is achieved in accordance with the invention in that for the formation of different layer images on the photosensitive element, the lens matrix is arranged to be displaceable with respect to the coded image plane, the position of the photosensitive element being adjustable within the depth of focus range of the lenses of the lens matrix.

When the lens matrix is displaced along the optical axis, for the display of different layer images, each time the distance changes between the object plane (film plane), that is to say the plane in which the coded image is situated, and the lens matrix, and hence the object distance. The image distance, i.e. the distance between the photosensitive element and the lens matrix, can be determined for each object distance by the lens formula and the known focal distance of the lenses which is the same for all lenses. By arranging the photosensitive element each time at an adapted distance from the lens matrix, sharp layer images of the object are always obtained. Because the depth of focus of the lenses has a given range, the foregoing is also applicable to distances which are slightly larger or slightly smaller than the image distance. For example, when the lens matrix is displaced step-wise, the object can be displayed layer-wise in each position of the lens matrix within the depth of focus range of the lenses, also in the so-called oblique layers.

In a preferred embodiment in accordance with the invention, the lens matrix and the photosensitive element are simultaneously and continuously displaced, the photosensitive element being continuously situated at a distance from the lens matrix which corresponds to the optimum image distance. As a result, the layer images are always reconstructed with optimum sharpness. The lenses of the lens matrix may also have a large aperture, and hence a small depth of focus range, so that large light intensity losses due to shielding are avoided. Sharp reproduction of even oblique layers is again possible within the depth of focus range.

Some embodiments of the invention will be described in detail hereinafter.

Figure 4:
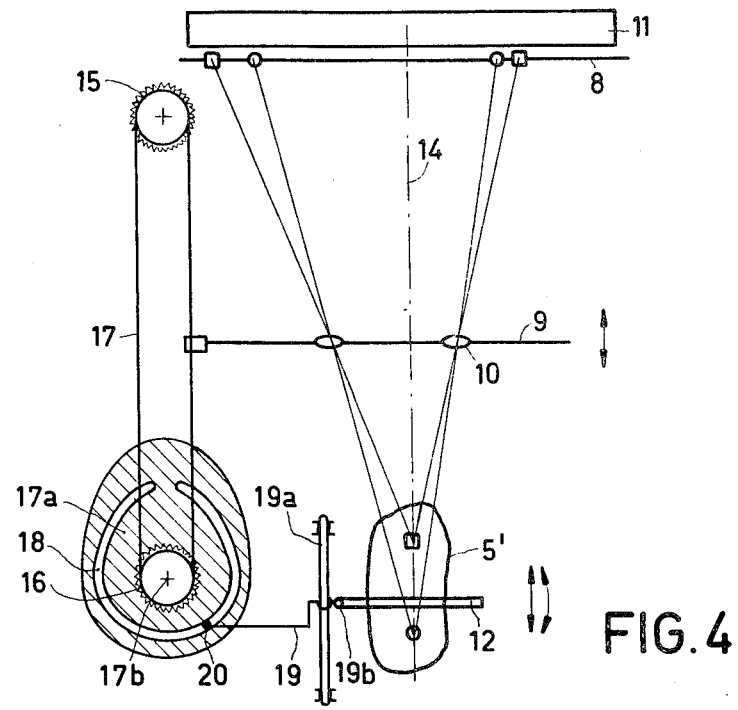
Figure 5:
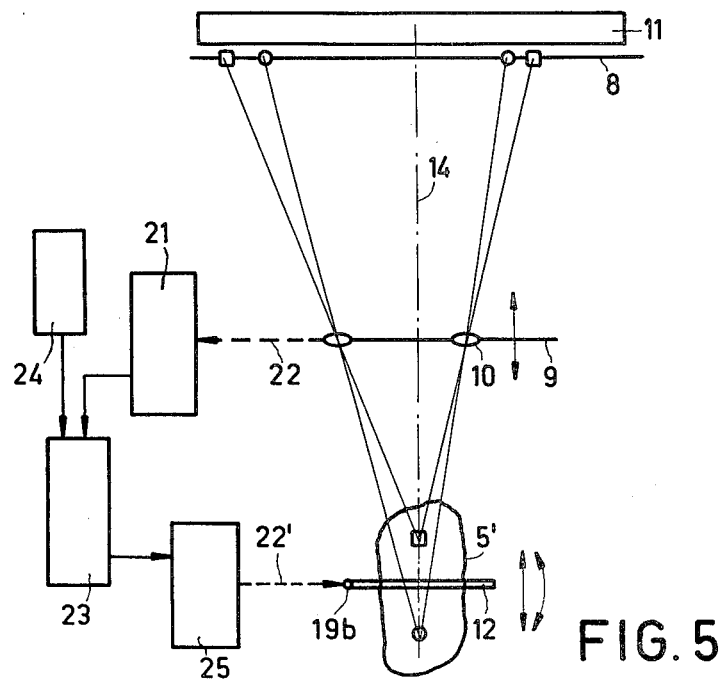
Figure 6:
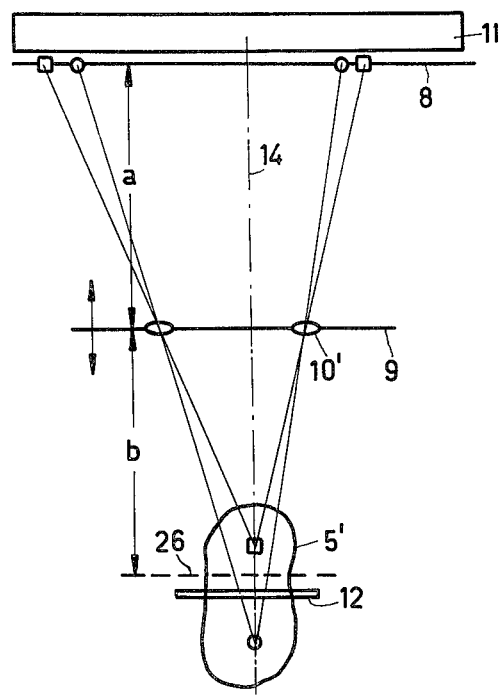

FIG. 4 shows a decoding device with a lens matrix and a photosensitive element which can be simultaneously and continuously positioned by means of a mechanical drive, FIG. 5 shows a decoding device with a lens matrix and photosensitive element which can be positioned by means of electrical adjusting means, and FIG. 6 shows a decoding device which comprises a movable lens matrix and a stationary radiation-sensitive layer.

Figure 1:
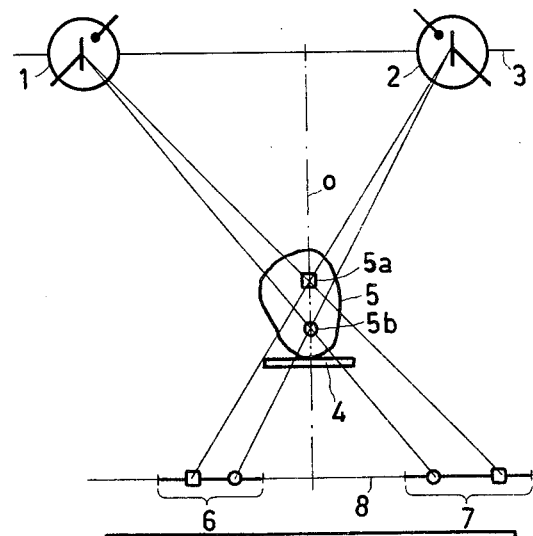
FIG. 1 shows a known device for irradiating an object from different directions.
Figure 2:
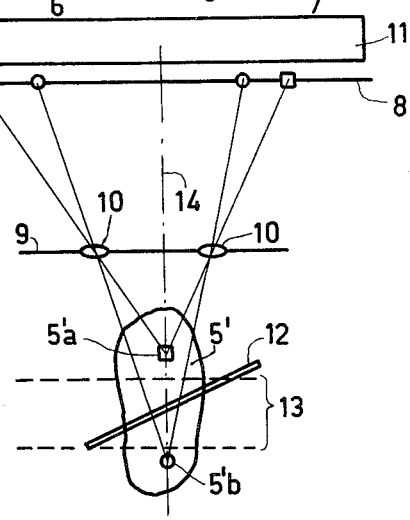
FIG. 2 shows a known decoding device with a stationary lens matrix.

FIG. 1 shows a known, fast tomosynthesis apparatus which comprises, for example, two X-ray tubes 1 and 2 which are arranged in a radiation source plane 3 and by means of which an object 5, for example, an organ of a human body situated on an examination table 4, is irradiated in order to record perspective images 6, 7 on a film 8, so that a coded image is obtained. It is shown that the structures 5a and 5b are adjacently projected from different layers of the object 5 in the image plane 8. From the perspective images 6 and 7, however, no direct conclusions can be drawn as regards the location of the structures 5a and 5b in the object 5. The separate layers of the object 5 can be reconstructed only by way of a decoding step. This can be realized in an optical manner, for example, by means of the decoding device shown in FIG. 2. Using a lens matrix 9, the lenses or lens systems 10 are arranged in accordance with the flat distribution of the X-ray tubes 1 and 2, the perspective images 6 and 7 which are arranged in front of a light box 11 and are illuminated thereby, are superposed. The lens matrix plane extends parallel to the film 8 and transversely of an optical axis 14 which corresponds to the optical axis 0 in FIG. 1. The lens matrix 9 forms the perspective images 6 and 7 at a scale of approximately 1:1, which means that each lens forms the same image. By superposition of all these images, a zone is formed in the image space of the lens matrix 9, in dependence of the depth of focus range of the lenses 10, in which all images are superposed to form a three-dimensional brightness distribution 5' which corresponds to the original three-dimensional object 5.

By displacement or rotation of, for example, a frosted glass plate 12, the entrance face of an image pick-up tube or a film (photosensitive detector faces), images can be formed of arbitrary layers, including oblique layers, i.e. layers which are not parallel to the matrix plane, in the reconstructed object 5'. In any arrangement this decoding method only enables sharp imaging of the object layers which are situated within a depth of focus range 13 of the lenses 10. The reconstruction of the layer images outside the depth of focus range 13 is unsharp. In the case of a large object 5, a large object volume 5' results, therefore, not all layers can be imaged with the same sharpness.

Figure 3:
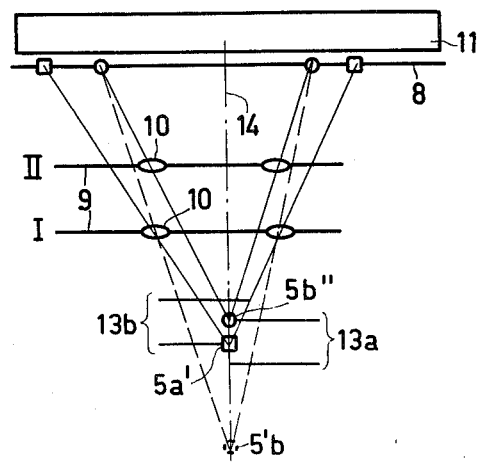
FIG. 3 shows a decoding device with a displaceable lens matrix.

FIG. 3, however, shows a decoding device which comprises a lens matrix 9 which is displaceable in the direction of the optical axis 14 which extends transversely of the matrix plane. For example, when the lens matrix 9 is in the position I, the object detail 5a' is reconstructed significantly nearer to the lens matrix 9 than the object detail 5b'. For example, the object detail 5a' is situated within the depth of focus range 13a of the lenses 10, while due to the extent of the depth of focus range 13a, the object detail 5b' is situated outside the depth of focus range 13a. The extent of the depth of focus range 13a is a function of the object distance, so the distance between the lens matrix 9 and the film 8. Thus, the object detail 5a, for example, can be sharply image on a frosted glass plate, while the image of the object detail 5b' is unsharp.

Also in order to enable sharp imaging of the object detail 5b', the lens matrix 9 is displaced to the position II in the direction of the film 8, until the object detail 5b' is situated within the depth of focus range 13b of the lenses 10 (5b"). In this depth of focus range 13b the frosted glass plate 12 is positioned again; and the object detail 5b" is then sharply imaged thereon.

The displacement of the lens matrix 9 can be realized, for example, intermittently. After each displacement, the object distance is determined. Subsequently, from the object distance and the focal distance of the lenses 10, the image distance is determined, i.e. the distance between the lens matrix 9 and the image plane thereof in which the object details are sharply imaged. The frosted glass plate 12 is then positioned at this distance. The frosted glass plate 12 can be moved, for example, continuously in the depth of focus range 13a and 13b, so within a given zone in front of and behind the image plane, for the formation of sharp layer images. Sharp images of oblique layers can thus also be obtained in the depth of focus range.

Obviously, the lens matrix 9 may also be continuously displaced. The frosted glass plate 12 is then also continuously displaced so that it is situated within the depth of focus range of the lens matrix in any position thereof. This means that the combined movement of the lens matrix 9 and the frosted glass plate 12 is such that each time the lens formula $1/f = 1/a + 1/b$, in which f is the focal distance of the lenses 10, a is the object distance and b is the image distance, is satisfied.

The continuous and coupled movement of the lens matrix 9 and the frosted glass plate 12 can be realized, for example, by means of a non-linear mechanical drive which comprises a cam disc. A drive of this kind is shown in FIG. 4. It consists of, for example, two sprockets 15 and 16 with an endless chain 17. The lens matrix 9 is connected to the chain 17 so that movement of the chain 17 causes displacement of the lens matrix in the direction of the optical axis 14, and parallel to the film 8. The sprocket 16 also supports a cam disc 17a which comprises a groove (or a slot) 18 which is engaged by a pin 20 which is connected to the frosted glass plate 12 by way of a mechanical system of rods 19. The groove 18 in the disc extends so that, when the cam disc 17a rotates around the axis 17b the lens matrix 9 moves, the frosted glass plate 12 is guided by the mechanical rod system 19 so that it is continuously situated within the depth of focus range of the lenses 10 of the lens matrix 9. To this end, the frosted glass plate 12 is guided along a guide rail 19a. For the display of different layer images, the observer merely has to displace the lens matrix 9, the frosted glass plate 12 automatically following this movement or vice versa. Images of oblique layers are formed by tilting the frosted glass plate each time around a pivot 19b (FIGS. 4, 5).

The continuous and coupled movement of the lens matrix 9 and the frosted glass plate 12, however, can also be realized by means of electromechanical adjusting means. To this end, the object distance a between the film 8 and the lens matrix 9 is measured by means of a detector 21, for example, a potentiometer. To this end, the lens matrix 9 is connected to the detector 21 by a system of rods 22. The measured object distance a is then applied to an arithmetic unit 23 which is electrically connected to the detector 21. The arithmetic unit 23 is also connected to a memory 24 in which the focal distance f of the lenses 10, being the same for all lenses 10, is stored. On the basis of the focal distance f and the object distance a, the arithmetic unit 23 subsequently determines the image distance b; this value is applied to an electromechanical adjusting member 25 which displaces the frosted glass plate, by a system of rods 22', each time to the correct position which corresponds to the image distance b.

FIG. 6 shows a further decoding device. In this device, however, the distance between the film 8 and the frosted glass plate 12 remains constant, only the lens matrix 9 being displaced in the direction of the optical axis 14, extending perpendicularly to the matrix plane and the film plane, for the formation of different layer images. The lenses 10' of the lens matrix 9 in any case have a larger depth of focus which is realized by the shielding on the lenses. However, this depth is substantially less than that of the lenses 10 in FIG. 2. The device is particularly suitable for decoding when the distance between the lens matrix 9 and the film 8 is first adjusted so that a mean object layer is sharply imaged with a scale of approximately 1:1 in the plane 26 of the lens matrix 9 during the decoding. This is achieved by selecting the double focal distance (2 f imaging) for the object distance a as well as for the image distance b. Obviously, the distances between the lenses 10' in the matrix plane must also be suitably chosen for realizing this 2 f imaging. Outside the image distance b, the frosted glass plate 12 is positioned so that it still forms a sharp image of a layer adjacent the mean object layer. When the lens matrix 9 is displaced during the decoding, the 2 f imaging is no longer adhered to. However, this means a displacement of the image plane 26 in the direction of the frosted glass plate 12 and finally beyond the frosted glass plate 12. This occurs when the lens matrix 9 is displaced with respect to the film 8 as well as when it is displaced with respect to the frosted glass plate 12. A comparatively large object zone which is sharply reconstructed then exists in front of and behind the frosted glass plate 12.

What is claimed is:

1. A device for examining the interior of a three-dimensional object comprising:

means including a plurality of radiation source positions in a single plane for forming a coded image of separate perspective images of an object, means including a lens matrix arranged parallel to the plane of said coded image for reconstructing said object by superposing said perspective images, said lens matrix having a lens distribution corresponding to a distribution of said radiation source positions, means including a displaceable photosensitive element in an image space for forming separate layer images of said object, said photosensitive element being adjustable within the depth of focus range of lenses in said lens matrix, and said lens matrix being displaceable with respect to said coded image plane for forming different layer images on said photosensitive element, wherein said lens matrix and said photosensitive element are displaceable in a coupled manner.

2. A device according to claim 1, wherein said lens matrix can be step-wise displaced.

3. A device according to one of claims 1 or 2, wherein said lens matrix and said photosensitive element are positioned by a mechanical drive.

4. A device according to claim 3, wherein said mechanical drive consists of a cam disc having a groove extending in the surface of said disc, said cam bisc being mechanically coupled to said lens matrix so that it rotates around an axis extending perpendicularly to said disc surface during displacement of said lens matrix, and a pin for engaging said groove and connected to said photosensitive element by a system of rods in order to position said photosensitive element in said depth of focus range during lens matrix displacement.

5. A device according to one of claims 1 or 2, wherein said lens matrix and said photosensitive element are positioned by electromechanical adjusting means.

6. A device according to claim 5, wherein said electromechanical adjusting means comprises a detector for measuring a distance a between said lens matrix and said coded image, a memory for storing a focal distance f, an arithmetical unit for determining the distance b between said photosensitive element and said lens matrix, and an adjusting member for providing corresponding displacement of said photosensitive element, and wherein an output of said detector and an output of said memory are connected to said arithmetical unit, said arithmetical unit being connected to said adjusting member.

* * * * *

UNITED STATES PATENT AND TRADEMARK OFFICE
CERTIFICATE OF CORRECTION

PATENT NO. : 4,383,733
DATED : MAY 17, 1983
INVENTOR(S) : HERMANN WEISS ET AL

It is certified that error appears in the above—identified patent and that said Letters Patent is hereby corrected as shown below:

Claim 4, Line 3 change "bisc" to --disc--.

Signed and Sealed this

Thirtieth Day of August 1983

[SEAL]

Attest:

GERALD J. MOSSINGHOFF

Attesting Officer    Commissioner of Patents and Trademarks